United States Patent [19]

Jain

[11] Patent Number: 5,312,378
[45] Date of Patent: May 17, 1994

[54] CURVED TRANSPARENT SURGICAL SHIELD

[76] Inventor: Krishna M. Jain, 8405 Plover, Kalamazoo, Mich. 49002

[21] Appl. No.: 713,690

[22] Filed: Jun. 11, 1991

[51] Int. Cl.$^5$ ............................................. A61M 1/00
[52] U.S. Cl. ................................. 604/317; 604/307; 128/910
[58] Field of Search .................. 128/910, 205.12, 849, 128/852, 854, 856, DIG. 6, DIG. 26; 604/268, 304, 307, 317, 326, 319, 263, 174, 170, 179, 180; 15/415.1, 339; 623/11

[56] References Cited

U.S. PATENT DOCUMENTS

| | | | |
|---|---|---|---|
| 2,246,404 | 6/1941 | Ross | 15/415.1 |
| 3,421,510 | 1/1969 | Kettenbach | |
| 3,435,827 | 4/1969 | Ericson | |
| 4,392,271 | 7/1983 | Sepke | 15/339 |
| 4,476,860 | 10/1984 | Collins et al. | 128/852 |
| 4,615,692 | 10/1986 | Giacalone et al. | 604/174 |
| 4,807,617 | 2/1989 | Nesti | 128/910 |
| 4,836,199 | 6/1989 | Palmer | 604/119 |
| 4,865,590 | 9/1989 | Marmar | 604/263 |

Primary Examiner—Randall L. Green
Assistant Examiner—Rob Clarke
Attorney, Agent, or Firm—Varnum, Riddering, Schmidt & Howlett

[57] ABSTRACT

A surgical splatter shield is provided which is adapted to be carried by a suction catheter for effecting the suction of blood from the area being operated on without the customary undesirable splatter of blood. The surgical splatter shield is preferably in the form of an elongated transparent plate which is transversely curved and which is attached to the customary suction catheter. The plate forming the surgical splatter shield has a sleeve permanently or fixedly attached to the edge of a central aperture. The sleeve extends upwardly from the plate and receives a terminal end of the suction catheter in press-fit or snug engagement.

10 Claims, 1 Drawing Sheet

CURVED TRANSPARENT SURGICAL SHIELD

This invention relates in general to new and useful improvements in surgical accessories, and more particularly to a surgical splatter shield for use with a suction catheter for restricting blood splatter during the removal of blood from the surgical theater.

BACKGROUND OF THE INVENTION

During vascular surgery, and particularly anastomosis where one vein is grafted into another vein, blood frequently fills the surgical cavity. It is necessary to use a suction catheter to remove blood from the surgical theater so the surgeon can see clearly in order to complete the anastomosis. A typical suction catheter comprises a substantially rigid, hollow plastic tube having an opening at the aspirator end. A plurality of radially-located openings are disposed near the end of the tube. In use, a vacuum is drawn in the tube and the material (primarily blood and other fluids) to be suctioned is introduced into the tube through the aspirator end and the radial openings. Frequently, however, while the suction catheter is operating, blood is spattered around the area, including the surgical team. There is a need for a device which will permit use of the suction catheter to keep the surgical theater clear, but will minimize undesirable splatter of blood and other fluids during such use.

SUMMARY OF THE INVENTION

The invention is directed to a shield or guard which will minimize the splatter that occurs when blood is suctioned from the operating theater during vascular surgery. The shield comprises an elongated plate, which is transversely curved about at least a single axis to form a concave surface and a convex surface. The convex surface defines a channel open at opposite ends and is dimensioned to receive a portion of a vein with the vein extending outwardly of the channel at the opposite ends. The concave surface is closely spaced from the vein after placement of the shield within the surgical field. The plate has an aperture surrounded by a sleeve extending from either the concave or convex surface. The aperture receives a suction catheter in tight engagement, whereby the splattering of blood from the surgical field is inhibited by the plate during vascular surgery. Preferably, the shield is transparent and has a radiopaque border for locating a lost splatter shield by x-ray.

Further in accordance with the invention, the aperture is centrally disposed on the plate and is defined by an annular edge. The sleeve can be permanently bonded to the plate in communication with the aperture. The sleeve can also be bonded to the plate at the annular edge and a terminal edge of the suction catheter can be snugly received within the sleeve.

With the above and other objects in view that will hereinafter appear, the nature of the invention will be more clearly understood by reference to the following detailed description, the appended claims, and the several views illustrated in the accompanying drawings.

DESCRIPTION OF INVENTION

Figure 1:
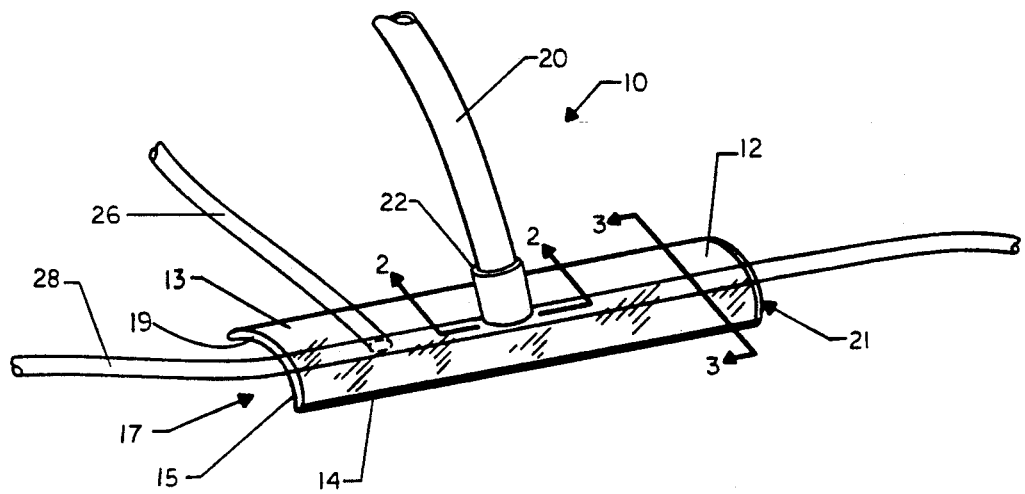
FIG. 1 is a perspective view of a suction catheter with the surgical splatter shield attached and schematically shown in place with respect to a blood vessel being grafted to another blood vessel.
Figure 2:
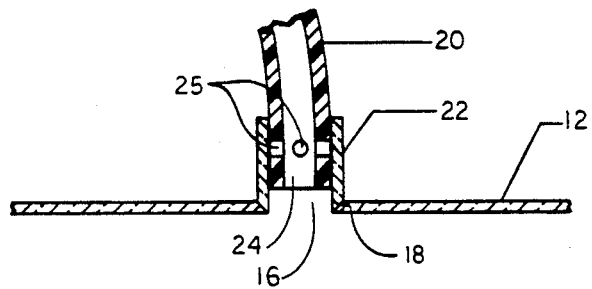
FIG. 2 is an enlarged fragmentary longitudinal sectional view taken generally along the line 2—2 of FIG. 1 and shows specifically the connection between the catheter and the plate.
Figure 3:
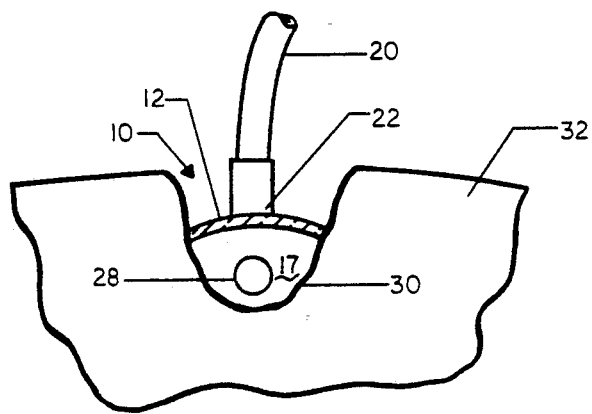
FIG. 3 is a schematic transverse vertical sectional view showing the plate generally positioned within a cavity and positioned for removing blood from such cavity relative to a blood vessel.

Reference is first made to FIGS. 1, 2 and 3 wherein there is illustrated a suction catheter and surgical splatter shield combination in accordance with this invention, the combination being generally identified by the numeral 10. The combination 10 includes a splatter shield 12 which is in the form of an elongated plate which is transversely curved. The shield or plate 12 generally varies in length between one and two inches. Typically the radius of curvature will be on the order of two to six millimeters.

The radius of curvature of the plate 12 defines a concave surface 13 and a convex surface 15. The convex surface 15 defines a channel 17 extending the length of the plate 12. The channel 17 is open at opposite ends 19, 21 of the plate 12. Preferably, the channel 17 is dimensioned to receive a portion of a vein 28 during vascular surgery. The vein can extend out the ends of the plate from the channel 17.

The plate 12 is formed of a transparent plastic material through which the suction operation may be readily viewed. The plate 12 is preferably provided with a radiopaque edge 14 which may be utilized to locate the plate 12 should it be lost during an operation. As is best shown in FIG. 2, the plate 12 is provided with a central hole or aperture 16 defined by an edge 18. A tower or sleeve 22 is adhered to the annular edge 18 for a purpose to be described.

Preferably, the plate 12 will be formed by extruding a tube of silicone elastomer and cutting out a section therefrom. The aperture 16 is die cut in the center of the plate 12 and then placed in an injection mold where the sleeve 22 is injection molded and adhered to the edge 18. The radiopaque edge may be formed by co-extruding about a 30 % concentration of barium sulfate with the tube. Preferably, a yellow colorant is added to identify the existence and location of the radiopaque edge.

A conventional suction catheter 20 will have a terminal end 24 and, near the terminal end, a number of apertures 25 disposed radially in the wall of the catheter. The terminal end 24 is snugly received in the sleeve 22 and frictionally held therein. Preferably, the sleeve 22 will cover the apertures 25 so the only ingress to the catheter is through the terminal end 24 and through the central aperture 16 in the plate 12.

Other connections between the catheter 20 and the plate 12 are possible within the spirit of the invention. For example, the sleeve may have an annular groove which receives the edge 18 in snap-fit engagement. Thus, the connection between this form of the sleeve and the plate 12 would permit rotation of the plate 12 relative to the suction catheter 20 so as to properly align the plate 12 in use with the surgical cavity.

Returning once again to FIG. 1, it will be seen that the surgical splatter shield or plate 12 has particular use in vascular surgery, especially where one vein 26 is being grafted to another vein 28.

Referring now to FIG. 3, the use of the suction catheter and surgical splatter shield combination 10 is best illustrated. A surgical cavity 30 is formed in the body 32 in conventional manner to provide access to the veins 26, 28 of which only the vein 28 is shown. As the surgical cavity begins to fill with blood during the surgical procedure, the blood must be removed by a suction catheter. The surgical splatter shield defined by the plate 12 is generally positioned within the surgical cavity 30 in overlying relation to the veins as shown (see also FIG. 1) and permits the suctioning of the excess blood from the surgical cavity 30 without undue splattering of blood out of the surgical cavity 30.

It will be readily apparent that in use, when it is necessary to suction blood away from the operating theater, the surgeon simply places the suction catheter and the attached shield over the vascular area to be suctioned. The transparency of the shield or plate enables the surgeon to observe and direct the suction process, and the shield itself will intercept blood and other fluids which would otherwise be splattered out of the operating theater by the suctioning.

Although only the preferred embodiment of the surgical splatter shield arrangement has been specifically illustrated and described herein, it is to be understood that minor variations in the surgical splatter shield and suction catheter combination may be made without departing from the spirit and scope of the invention as defined by the appended claims.

The embodiments of the invention in which an exclusive property or privilege is claimed are defined as follows:

1. A shield for use with a suction catheter within a surgical field during vascular surgery, said shield comprising:
    an elongated transparent plate, said plate being transversely curved about at least a single axis to form a concave surface and a convex surface defining a channel open at opposite ends thereof and dimensioned to receive a portion of a vein therewithin with the vein extending outwardly of the channel at said opposite ends and with said concave surface closely spaced from said vein after placement of the shield within the surgical field, and having an aperture extending therethrough,
    and a sleeve surrounding the aperture and extending from one of the concave and convex surfaces for receiving a suction catheter in tight engagement whereby to inhibit splatter of blood and other fluids out of the surgical field during aspiration by the suction catheter during vascular surgery.

2. A shield according to claim 1 wherein said plate has a radiopaque border for locating a lost shield by x-ray.

3. A shield according to claim 1 wherein said aperture is disposed centrally in the plate.

4. A shield according to claim 3 wherein said aperture is defined by an annular edge.

5. A shield according to claim 3 wherein said sleeve is permanently bonded to said plate in communication with the aperture.

6. A shield according to claim 4 wherein said sleeve is permanently bonded to said plate at the annular edge and a terminal edge of a suction catheter can be snugly received within the sleeve.

7. A surgical shield for use with a suction catheter within a surgical field during vascular surgery, said shield comprising a transparent elongated plate, said plate being transversely curved about at least a single axis to form a concave surface and a convex surface and having a width sized to extend partially around the circumference of a vein with the plate closely spaced from the vein after placement of the shield within the surgical field, and said plate having attaching means for attaching a suction catheter thereto for producing a vacuum below said plate, said attaching means comprising an opening through said plate and an integral tubular member extending from the convex surface, whereby when the suction catheter is used to aspirate blood and other fluids during vascular surgery, the shield is placed within the surgical field with the single axis generally aligned with the veins so as to inhibit the splatter of blood and other fluids during surgery.

8. A shield according to claim 7 wherein a suction catheter forms a permanent extension of said tubular member.

9. A shield according to claim 7 wherein said suction catheter extends into an upper end of said tubular member and is permanently secured to said tubular member.

10. A shield according to claim 7 wherein said plate has a radiopaque border for locating a lost shield by x-ray.

* * * * *